(12) United States Patent
Gramann et al.

(10) Patent No.: US 8,814,738 B2
(45) Date of Patent: Aug. 26, 2014

(54) DEVICE FOR DISPENSING A DENTAL COMPOSITION

(75) Inventors: Jens Gramann, Gräfelfing (DE);
Manfred Harre, Landsberg am Lech (DE); Ralf Kelz, Seefeld (DE);
Christian A. Richter, Feldafing (DE);
Karin Watzek, Kaufbeuren (DE);
Oezcan Doenmez, Landsberg am Lech (DE)

(73) Assignee: 3M Innovative Properties Company, St. Paul, MN (US)

( * ) Notice: Subject to any disclaimer, the term of this patent is extended or adjusted under 35 U.S.C. 154(b) by 61 days.

(21) Appl. No.: 13/510,550

(22) PCT Filed: Nov. 17, 2010

(86) PCT No.: PCT/US2010/056959
§ 371 (c)(1),
(2), (4) Date: Aug. 3, 2012

(87) PCT Pub. No.: WO2011/062948
PCT Pub. Date: May 26, 2011

(65) Prior Publication Data
US 2012/0292341 A1    Nov. 22, 2012

(30) Foreign Application Priority Data

Nov. 20, 2009    (EP) .................................... 09176601

(51) Int. Cl.
*F16H 1/32*    (2006.01)
(52) U.S. Cl.
USPC ....................................................... 475/165

(58) Field of Classification Search
USPC ................ 475/165, 180; 222/137, 145.6, 390
See application file for complete search history.

(56) References Cited

U.S. PATENT DOCUMENTS

| | | |
|---|---|---|
| 1,413,982 A | 4/1922 | Gill |
| 1,502,936 A | 7/1924 | Borroughs |
| 1,572,837 A | 2/1926 | Betts |
| 2,485,467 A | 7/1946 | Weisbaum |
| 2,630,022 A | 3/1953 | Terdina |
| 2,942,293 A | 6/1960 | Wahl |
| 3,108,487 A | 10/1963 | Sandler |
| 3,134,275 A | 5/1964 | Davison |
| 3,225,626 A | 12/1965 | Geyer |
| 3,449,971 A | 6/1969 | Posh |
| 3,469,463 A * | 9/1969 | Ishikawa .......................... 74/640 |
| 3,530,734 A | 9/1970 | Wray |
| 4,180,187 A | 12/1979 | Ben-Haim |
| 4,390,115 A | 6/1983 | Bigham |
| 4,614,128 A | 9/1986 | Fickler |

(Continued)

FOREIGN PATENT DOCUMENTS

| | | |
|---|---|---|
| DE | 2005017149 | 10/2006 |
| DE | 102005017149 | 10/2006 |

(Continued)

*Primary Examiner* — Edwin A Young

(57) ABSTRACT

A device for dispensing a dental composition comprises a piston for extruding a component of the dental composition from a container. The device has a roller drive for displacing the first piston. The roller drive comprises cooperating first and second rollers, and each of the rollers have a roller surface with a radial rib profile. The rollers are arranged for rolling with their roller surfaces on one another. The invention may help providing for a relatively reliable and compact device.

17 Claims, 9 Drawing Sheets

(56) References Cited

U.S. PATENT DOCUMENTS

| | | | |
|---|---|---|---|
| 4,811,619 | A | 3/1989 | Cutburth |
| 4,827,789 | A | 5/1989 | Hallidy |
| 4,898,249 | A | 2/1990 | Ohmori |
| 4,908,017 | A | 3/1990 | Howson |
| 4,944,639 | A | 7/1990 | Washington |
| 5,058,781 | A | 10/1991 | Aronie |
| 5,104,005 | A | 4/1992 | Schneider, Jr. |
| 5,176,646 | A | 1/1993 | Kuroda |
| 5,207,357 | A | 5/1993 | Aronie |
| 5,242,082 | A | 9/1993 | Giannuzzi |
| 5,269,762 | A | 12/1993 | Armbruster |
| 5,351,797 | A | 10/1994 | Lawson |
| 5,464,128 | A | 11/1995 | Keller |
| 5,477,987 | A | 12/1995 | Keller |
| 5,788,008 | A | 8/1998 | Fort |
| 5,807,334 | A | 9/1998 | Hodosh |
| 5,816,445 | A | 10/1998 | Gardos |
| 5,860,739 | A | 1/1999 | Cannon |
| 5,911,343 | A * | 6/1999 | Keller .................. 222/145.1 |
| 6,158,295 | A | 12/2000 | Nielsen |
| 6,168,052 | B1 | 1/2001 | Keller |
| 6,311,871 | B1 | 11/2001 | Binder |
| 6,315,164 | B1 | 11/2001 | Mühlbauer |
| 6,348,022 | B1 | 2/2002 | Jin |
| 6,386,396 | B1 | 5/2002 | Strecker |
| 6,488,180 | B1 | 12/2002 | Bayat |
| 6,599,293 | B2 | 7/2003 | Tague |
| 6,837,612 | B2 | 1/2005 | Bublewitz |
| 6,889,872 | B2 | 5/2005 | Herman |
| 2004/0055404 | A1 | 3/2004 | Mills |
| 2006/0283885 | A1 | 12/2006 | Dolman |
| 2007/0072146 | A1 | 3/2007 | Pierson |
| 2007/0249453 | A1 * | 10/2007 | Sugitani .................. 475/4 |
| 2008/0034907 | A1 | 2/2008 | Gist, Jr. |
| 2008/0064553 | A1 * | 3/2008 | Newton .................. 475/165 |
| 2008/0261170 | A1 | 10/2008 | Ploy |
| 2008/0267005 | A1 | 10/2008 | Reinprecht |

FOREIGN PATENT DOCUMENTS

| | | |
|---|---|---|
| DE | 102008036643 | 2/2010 |
| EP | 1657804 | 5/2006 |
| EP | 1834603 | 9/2007 |
| WO | WO 2009/063509 | 5/2009 |

\* cited by examiner

DEVICE FOR DISPENSING A DENTAL COMPOSITION

CROSS REFERENCE TO RELATED APPLICATIONS

This application is a national stage filing under 35 U.S.C. 371 of PCT/US2010/056959, filed Nov. 17, 2010, which claims priority to European Patent Application No. 09176601.4, filed Nov. 20, 2009, the disclosures of which are herein incorporated by reference in their entirety.

FIELD OF THE INVENTION

The invention relates to a device for dispensing a dental composition. In particular the invention relates to a device comprising a piston for extruding at least a component of the dental composition from a first container, and a roller drive for displacing the first piston.

BACKGROUND ART

For preparation of dental compositions in a dental practice dispensing devices are often used for automatic dispensing the compositions from bulk containers. Such dispensing devices typically are used to prepare the compositions in a relatively short time and at a desired quality. Further there are dispensing devices that allow for automatic mixing of components to form the dental composition.

Some dental compositions, for example dental impression materials, have a relatively high viscosity so that for a rapid dispensation of such materials relatively powerful devices are required. Typically such devices for dispensing a dental composition have one or more plungers that can be advanced by motor power for extruding the composition from one or multiple containers. Therefore a variety of devices have been provided which have powerful motors, robust plunger drive mechanisms and which overall are designed relatively mechanically stable.

For example EP 1 010 401 A1 discloses a device for providing a dental multi-component compound. The device has pistons for advancing components from cartridges into a mixer which can be displaced relative to the components by a threaded spindle. For driving the spindle the device has a geared motor which is coupled to the spindle via a belt transmission. The device has a further motor for driving the mixer.

Although available devices on the market may provide certain advantages there is still a desire to provide a design of such a device that allows for manufacturing at minimized costs. Further such a device is desirably adequate for use in a dental practice and further relative reliable.

SUMMARY OF THE INVENTION

In one aspect the invention relates to a device for dispensing a dental composition. The device comprises a first piston for extruding at least a component of the dental composition from a first container, and a roller drive for displacing the first piston. The roller drive comprises a first roller and a cooperating second roller, each of the first and the second rollers having a roller surface comprising a radial rib profile. Further the first roller has a first longitudinal axis and the second roller has a second longitudinal axis with the first and second longitudinal axes being arranged in an off-center relationship relative to one another. The first and second rollers are arranged for rolling with their roller surfaces on one another with the rib profiles engaging. The first and second rollers are preferably further arranged such that the rib profiles axially guide or restrain the first and second rollers relative to one another. The axial restraint may however nevertheless enable an axial displacement of the first and second rollers relative to one another, for example due to the first and second rollers being caused to roll with their roller surfaces on one another.

The first and second rollers may further be arranged for rolling with their roller surfaces directly, for example without a further component arranged between, on one another The invention may be advantageous in that it allows a relatively simple and compact design of the device. In particular complex gear boxes may not be required. A design which is enabled by the invention may further help maximizing the use of standardized components as they may be available in the industry. For example a standard motor providing a standard rotation speed of for example 1500 l/min or even 3000 l/min may be used in the device in combination with a transmission having only a few gears. The invention may further be advantageous in that it may enable relatively slow or extremely slow extrusion speeds of the composition. The invention may also allow the device to provide relatively high extrusion forces for extruding the dental composition. This may allow the dispensation of relatively high viscous compositions for example. Further the invention preferably provides for a relatively uniform extrusion speed of the composition, and may in particular minimize stick slip effects in the displacement of the piston. The invention may help minimizing the power consumption of the device and thus may allow for using less powerful motors than devices of the prior art. Further the invention may help minimizing the number of parts used for making the device, and in particular for making the drive for displacing the piston.

In one embodiment the first and second rollers are adapted such that rolling of the first and second rollers with their roller surfaces on one another causes the first and second rollers to displace in a direction laterally to a direction of the rolling. For example the rolling causes the first and second rollers to displace axially to at least one of the longitudinal axes. Such a displacement may be used to displace the piston of the device and is further referred to simply as "axial displacement".

In one embodiment the rib profile of at least one of the first and second rollers is formed by a screw thread. For example the rib profile of one of the first and second rollers may be formed by a screw thread and the other one of the first and second rollers may be formed by at least one closed circumferential rib. The rib may be arranged radially around the roller and closed (like a ring, for example). The rib profile may further be formed by a plurality of closed circumferential ribs. The closed ribs and the thread when rolling on each other due to the pitch of the thread may provide for the axial displacement.

In another embodiment the rib profile of the first roller and the rib profile or the second roller each are formed by a screw thread. The threads when rolling on each other due to the pitches of the thread may provide for a displacement the first and second rollers relative to one another and laterally to a direction of the rolling. The threads of the first and second rollers may have different pitches. Further the roller drive may have first and second rollers having cooperating right-hand and left-hand threads. The right-hand and left-hand threads may have different pitches such that when the threads roll on each other an axial displacement id provided. For example if the pitches are similar, but still differentiate, a very slow axial displacement may be achieved. The embodiment implementing cooperating right-hand and left-hand threads preferably have non-equal pitches.

In one embodiment the roller surfaces of the first and second rollers have different circumferences. For example the first roller surface may have a first diameter and the second roller surface may have a cooperating second thread diameter, wherein the first and second diameters are different. The diameter of the first or second roller may correspond to an effective diameter or flank diameter of the rib or thread which is preferably the mean diameter between a major and a minor rib or thread diameter. Thus the roller surfaces may be approximately cylindrical (although the lateral cylinder surface may be structured to form the rib or thread) with the cylinders having different diameters. By the difference in the circumferences a transmission ratio between the first and the second rollers may be determined. Therefore the roller drive may be provided with a speed reduction allowing for one of the first and second rollers to be driven at a relatively high speed, whereby nevertheless a relatively slow axial displacement may be achieved. Thus an additional gear box may be made unnecessary.

In one embodiment the first and second longitudinal axes are arranged generally parallel relative to one another. The first and second rollers may therefore be in an epicyclic or a planetary roller arrangement. This may allow a relatively simple design of a roller drive that provides for a speed conversion from one to another roller.

One aspect of the invention relates to a device for dispensing a dental composition which comprises a first piston for extruding at least a component of the dental composition from a first container, and a roller drive for displacing the first piston. The roller drive comprises a first roller and a cooperating second roller. Each of the first and the second rollers have a thread which provides a roller surface. Further the first roller has a first longitudinal axis and the second roller has a second longitudinal axis. The device is adapted such that the roller drive can be operated in a first operating mode and a second operating mode. In the first operating mode the screw and the nut are positioned with the first and second longitudinal axis arranged in an off-center relationship relative to one another, and with the first and second rollers arranged for (preferably predominantly) rolling with their roller surfaces on one another. Further in the second operating mode the screw and the nut are positioned with the first and second longitudinal axis substantially arranged in a center relationship relative to one another, and with the first and second rollers arranged for (preferably predominantly) sliding with their roller surfaces on one another. In the first and second operating modes the threads engage one another.

The roller drive thus is formed by a threaded screw and a threaded nut that are adapted to be screwed with one another. The threads of the screw and the nut preferably are dimensioned such that the smallest inner diameter of the thread of the nut is smaller than the largest outer diameter of the thread of the screw. Further the threads of the nut and the screw are preferably dimensioned in diameter to form a play between. In the first operating mode the nut and the screw are preferably forced toward each other in a direction radially to at least one of the longitudinal axes, and in the second operating mode the radial force is reduced or suspended relative to the first operating mode. In the first operating mode the roller drive preferably operates such that the threads of the screw and the nut predominantly roll on each other, whereas in the second operating mode the roller drive preferably operates such that the threads predominantly slide on each another. Thus in the first operating mode the axial displacement speed of the screw and the nut relative to each other is preferably smaller than the axial displacement speed in the second operating mode at the same rotation speed of the screw and the nut relative to each other.

In this embodiment the device preferably has a forcing mechanism for forcing the screw and the nut in the direction radially to the at least one of the longitudinal axes. The forcing mechanism may comprise a spring, a pneumatic actuator (like a pneumatic cylinder), a hydraulic actuator, a magnetic actuator, a weight, or any other structure suitable to exert mentioned force. The forcing mechanism is preferably controllable to establish the operation of the roller drive in the first or the second operating mode.

In one embodiment the first roller has an outer rib profile, for example a thread, and the second roller forms a hollow roller with an inner rib profile or thread. The first roller may form a planetary roller within the hollow second roller. This means that in this embodiment the first roller may be arranged eccentrically within the second roller with the rib profiles engaging. This may provide for relatively compact design of the roller drive providing nevertheless a relatively high extrusion force.

In another embodiment the first and second rollers both have an outer rib profile, wherein the first roller forms a sun roller and the second roller forms a planetary roller around the sun roller. Thus the first and second rollers may be arranged side by side with the rib profiles engaging. The device may further have at least one, preferably at least two, further planetary rollers. This may allow the rollers to guide each other so that the roller drive may also serve as a linear guidance. Therefore a device implementing the roller drive of this embodiment may not need an additional linear guidance, for example for guiding the piston.

In one embodiment the device comprises at least one of a belt, a chain and a push-pull chain for transmitting a displacement of the roller drive to cause the piston to displace. A belt or chain may for example be pulled by the roller drive to pull the piston in a certain direction, for example to advance the piston toward the composition for extrusion. The piston may further be connected to a return spring for retracting the plunger. Further two belts, chains or a combination may be used, for example one for advancing the piston and another one for retracting the piston. In another embodiment the piston may be displaced by the roller drive via a push-pull chain being adapted to transmit pulling and pushing forces. Therefore the device of the invention may be designed relatively compact because a belt or (push-pull) chain may allow placing the roller drive to a variety different location in the device.

In a further embodiment the device comprises a second piston for extruding a second component from a second container. The device is preferably adapted to receive and drive a dynamic mixer for continuously mixing the first and second component as they are extruded from the first and second containers. Further the device may have a motor for driving the roller drive and a mixer shaft for driving the mixer. The device may comprise one roller drive for driving the first and the second pistons. Further the device may comprise two roller drives each for driving one of the first and second pistons.

In one embodiment the components of the composition may be provided in containers, for example ones that can be exchanged or refilled in the device. The device may therefore have a receptacle for receiving the containers, for example a receptacle allowing for the containers to be replaced by other containers. Further the containers may have outlets from which the components may be dispensed. Preferably the device is adapted such that the pistons for extruding the components can be advanced in a direction toward the components. Further the device is preferably adapted such that the pistons can be retracted from the components. This may allow for example removing the pistons from the containers so that the containers can be refilled or replaced. Further retracting the pistons from the components after dispensing may help avoiding afterflow of the mixed composition due to the pistons maintaining a pressure applied on the components. The roller drive is preferably capable of converting a rotation from a motor or motors in the device in a generally linear displacement that is usable to advance and/or retract the pistons. The device, and in particular the roller drive, may be adapted such that the forces of between about 4000 N and about 6500 N, for example, can be applied to the components for extrusion.

Another aspect of the invention is directed to a use of a roller drive in combination with a dispensing device for dental composition. A roller drive may provide for a relatively constant displacement of a piston or pistons of the device and thus may provide for a relatively reliable mixing quality of the mixture from the components.

DETAILED DESCRIPTION OF THE INVENTION

Figure 1:
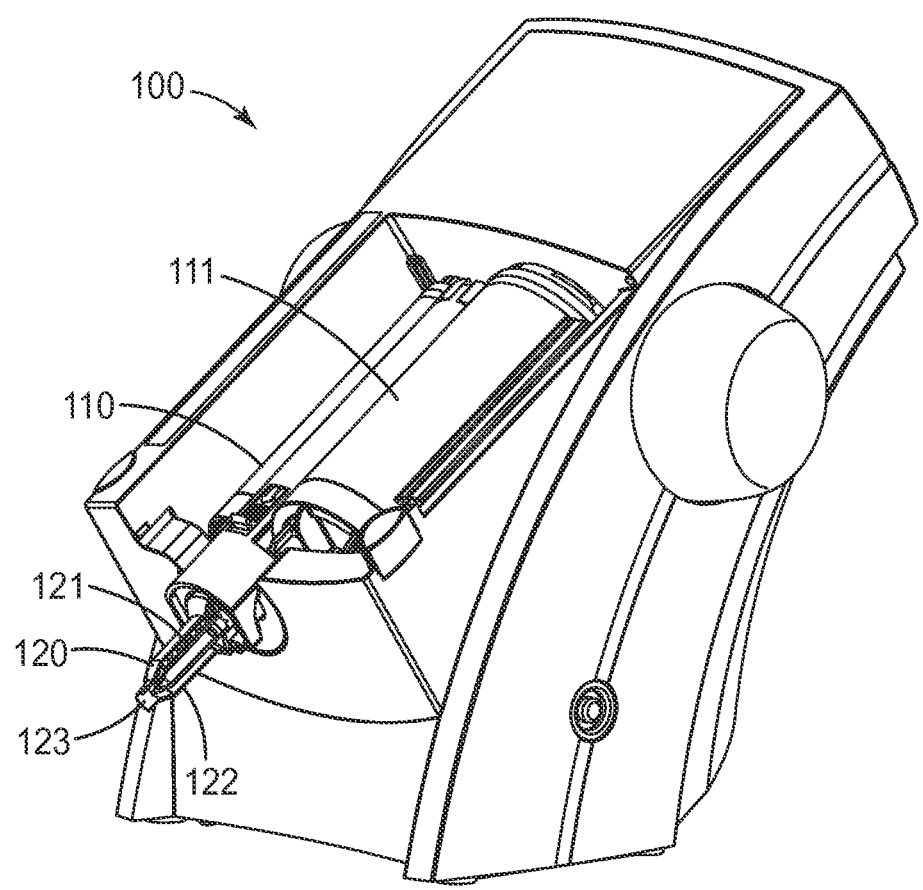
FIG. 1 is a perspective view of a device for dispensing a dental composition according to an embodiment of the invention.

FIG. 1 shows a device 100 for mixing and dispensing dental compositions. The device is motorized and therefore allows for automatic dispensation of the compositions. A similar device is available under the designation 3M™ ESPE™ Pentamix™ from 3M ESPE AG, Germany. The device 100 holds two components of a dental composition in containers 110, 111. A mixer 120 for mixing the two components is attached to the device 100. The mixer 120 has a mixing chamber formed between a rotatable mixing rotor 121 and a mixer housing 122. The mixer is connected with the containers 110, 111 such that the individual components can flow into the mixing chamber. The mixture can exit through an outlet 123 of the mixer 120. The device 100 is adapted to drive the mixing rotor 121 so as to mix the components in the mixing chamber. The device 100 implements a continuous dynamic mixing process in which components can be continuously supplied into the mixing chamber and in which the mixture from the components can be dispensed continuously from the mixer. Thus the device allows preparation for variable amounts of dental compositions without the need of pre-determining amounts of initial components of the mixture. The components can be advanced toward the mixer 120 by a piston (not shown) of the device 100. Both the mixer and the piston can be driven by a motor, or individual motors, in the device 100.

The device shown may be used to mix and dispense a hardenable dental impression material, for example. The mixed material may be used to fill a dental tray which is then placed into a patient's mouth to take a dental impression. The mixer is attached replaceably at the device 100. Therefore when the mixed material hardens and thus blocks the mixer the used mixer may be replaced by an unused mixer for the next use of the device.

Figure 2:
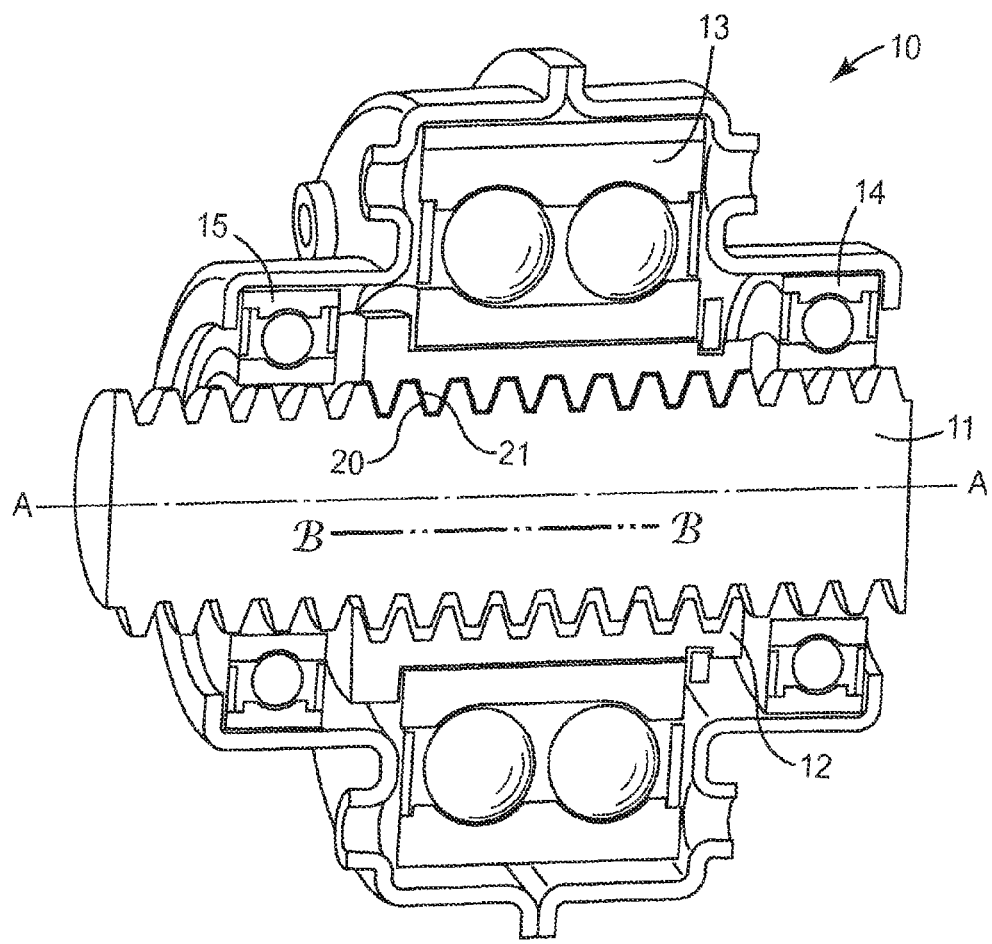
FIG. 2 is a cross-sectional perspective view of a roller drive according to an embodiment of the invention.

FIG. 2 shows a roller drive 10 having a first roller in the form of a threaded screw 11 or spindle and a second roller in the form of a hollow threaded nut 12. The screw 11 and the nut 12 are sized such that a play is provided between the nut 12 and the screw 11 when mated. The screw 11 has a longitudinal axis A which in the example may be a rotation axis of the screw 11, and the nut 12 has a longitudinal axis B which may be a rotation axis of the nut 12. The longitudinal axes A, B are arranged parallel offset from one another. Therefore the screw 11 and the nut 12 are arranged in an off-center relationship relative to one another. The threads of the screw 11 and the nut 12 form roller surfaces 21, 20, respectively, which due to the off-center arrangement of the screw 11 and the nut 12 relative to one another are in contact with each other. Further the screw 11 and the nut 12 are radially restrained by bearings 13, 14, 15 relative to one another such that the roller surfaces 21, 20 of the screw 11 and the nut 12 are maintained in contact with one another (or urged towards contacting each other). That is, the screw 11 and the nut 12 are arranged relative to one another such that the off-center relationship is maintained. Therefore a rotation of one of the screw 11 and the nut 12 is transmitted via the contacting roller surfaces 21, 20 by friction to the other one of the screw 11 and the nut 12. Thus the roller surfaces 21, 20 can roll on each other. This means that, in operation of the roller drive, in a contact area of the roller surfaces the roller surfaces 21, 20 preferably substantially do not slide on each other, or at least that rolling predominates sliding. This is in contrast to a screw and a nut being rotated relative to one another based on cooperating surfaces sliding relative to one another.

Due to the threads of the screw 11 and the nut 12 engaging with one another the screw and the nut are axially restrained against free axial (in a direction of the longitudinal axis A or B) displacement relative to one another. However an axial displacement of the screw and the nut relative to each other may be caused by a movement of the screw and the nut such that the roller surfaces roll on each other. This is explained in more detail in FIGS. 3, 4 and 5a through 5e.

Figure 3:
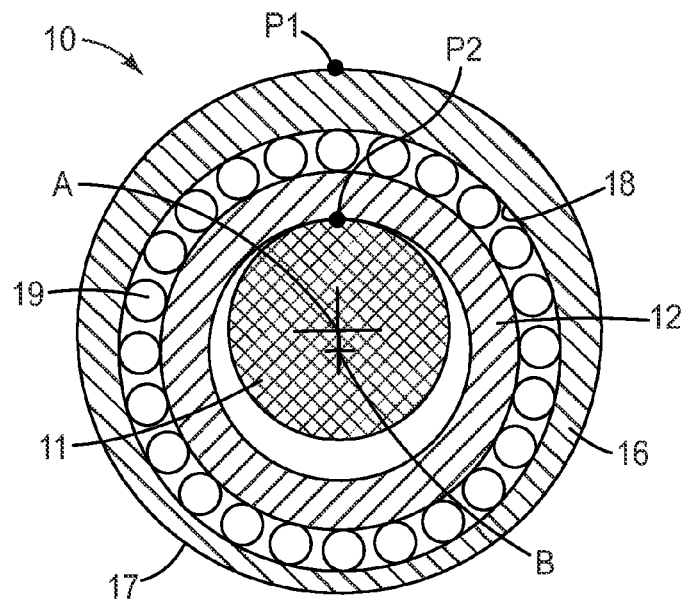
FIG. 3 is a schematic cross-sectional view of the roller drive shown in FIG. 2 in an initial stage of operation.

FIG. 3 is a cross-sectional view of the roller drive 10 of the invention. The screw 11 and the nut 12 are arranged in an off-center relationship to one another. For better clarity the threads are simplified by circular structures in the cross-sectional view although another structure would more appropriately represent the actual shape of the threads.

The screw 11 may be radially guided such that it generally cannot move radially, and may be further retained or locked against rotation. The nut 12 is guided rotatably about axis B within an outer ring 16. In the example the outer ring has an outer circular surface 17 which is arranged generally concentric with the axis A of the screw 11. Further the outer ring 16 has an inner circular surface 18 which is in an off-center relationship to the outer surface 17 and the axis A. The nut 12 is guided within the inner surface 18 via balls 19 and thus is guided or restrained in an off-center position relative to the axis A and the screw 11.

The operation of the roller drive is illustrated by help of a (virtual) first point P1 which is indicated on the outer surface 17 of the outer ring 16, and a (virtual) second point P2 indicated on the roller surface of the nut 12. In an initial position of the roller drive the first and second points P1, P2 are arranged on a vertical through the axis A.

Figure 4:
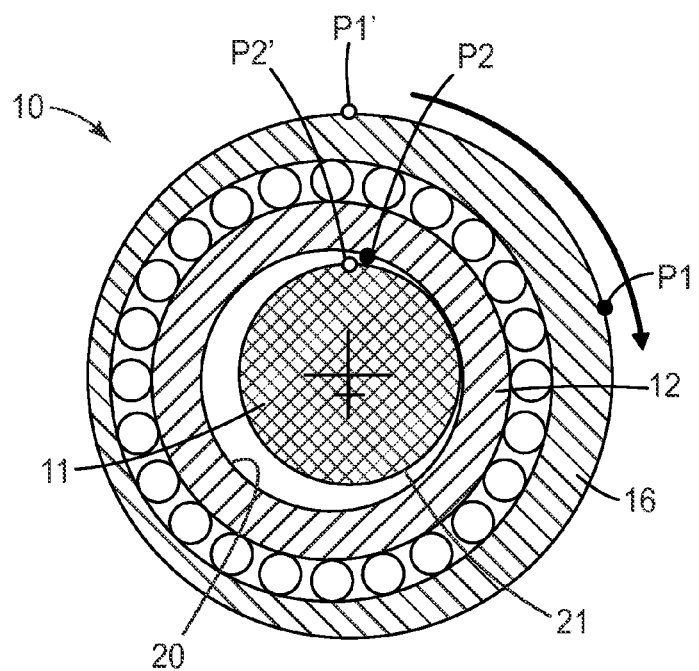
FIG. 4 is a schematic cross-sectional view of the roller drive shown in FIG. 3 at another stage in operation.

FIG. 4 illustrates the roller drive 10 with the outer ring 16 positioned by about 90° clockwise relative to the situation illustrated in FIG. 3. The point P1 indicates a new position of the outer ring 16 relative to the initial position P1'. This results from the nut 12 having moved from the initial position to the new position on a circle about the axis A. This planetary or epicyclic movement is caused by the roller surface 20 of the nut 12 and the roller surface 21 of the screw having rolled on each other while the outer ring 16 has rotated relative to the nut 12. The point P2 indicates new position of the nut 12 relative to the initial position P2'. The nut 12 relative to the initial position has rotated by a small angle about its rotation axis B. Therefore the nut 12 and the screw 11 in the position shown in FIG. 4 are rotated relative to one another in comparison to the situation illustrated in FIG. 3. As a result the screw 11 and the nut 12 in the situation shown in FIG. 4 due to the engaging threads are axially displaced relative to one another in comparison to the situation illustrated in FIG. 3. The rotation angle of the outer ring 16 is greater than the rotation angle of the nut during the operation illustrated in FIGS. 3 and 4. Therefore a rotation speed reduction between the outer ring 16 and the nut 12 is provided. This may allow for achieving a relatively slow axial displacement between the screw 11 and the nut 12 although the outer ring may be rotated at a relatively high rotation speed. As an advantage a standard motor providing for a relatively high standardized rotation speed may be used with the roller drive 10, and an additional gear box may be made unnecessary.

Figure 5A:
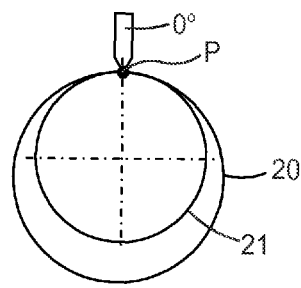
FIGS. 5a-5e are schematic cross-sectional views illustrating the operation of the roller drive shown in FIG. 2.
Figure 5B:
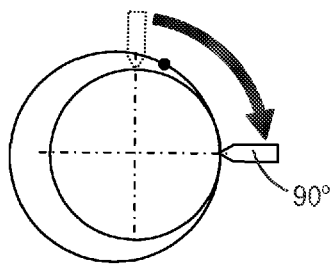
Figure 5C:
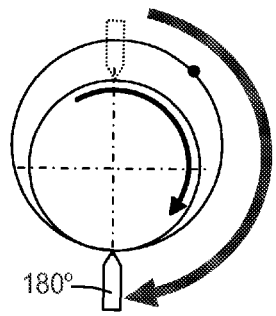
Figure 5D:
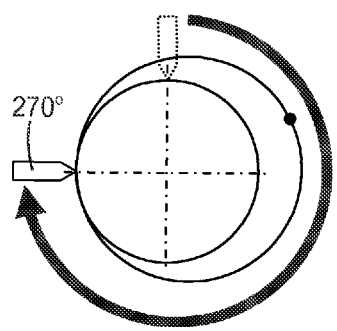
Figure 5E:
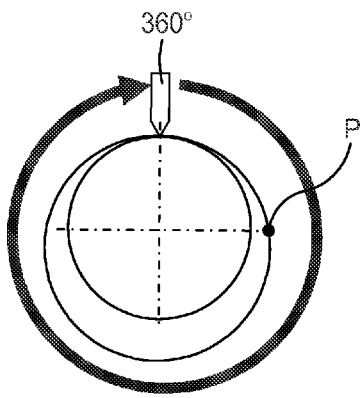

FIGS. 5a through 5e illustrate the movement of the roller surface 20 of the nut (not shown in detail) in response of a 360° rotation of the outer ring (not shown in detail). FIG. 5a illustrates the initial position in which a virtual point P is positioned at 0°. FIGS. 5b through 5d illustrate positions during a clockwise movement of the outer ring at 90°, 180° and 270°. FIG. 5e shows the outer ring positioned at 360°. This position corresponds to the position shown in FIG. 5a, but with the point P being positioned by about 90° clockwise relative to the initial position. Therefore in the example a rotation of the outer ring by 360° causes a rotation of about 90° of the nut so that the reduction is about 1:4 in ratio. In the example the roller surface 21 (indicated in FIG. 5a) has a first circumference and the roller surface 20 has a greater second circumference. The skilled person will recognize that other speed conversions may be implemented by selecting the first and second circumferences appropriately.

Figure 6:
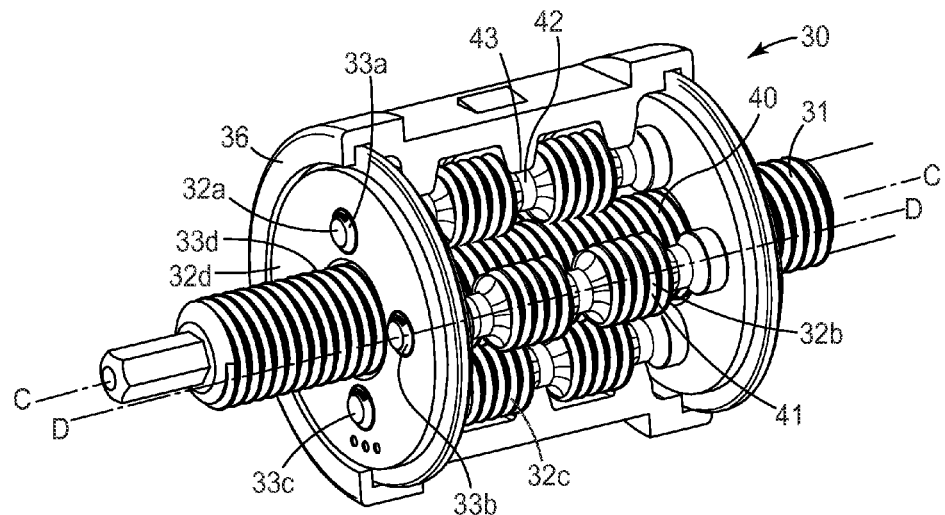
FIG. 6 is a cross-sectional perspective view of a roller drive according to a further embodiment of the invention.

FIG. 6 shows as another embodiment of the invention a roller drive 30 having a first roller in the form of a first threaded screw 31 or spindle and a second roller in the form of a second threaded screw 32a. In the example the second threaded screw and further screws 32b, 32c and 32d are arranged in a planetary arrangement relative to the first screw 31. An outer ring 36 surrounds the first and second screws 31, 32a as well as the further screws 32b, 32c, 32d. Although the roller drive 30 may operate without the presence of the further screws 32b, 32c and 32d, the further screws 32b, 32c and 32d may provide for concentric guiding the screw 11 and the outer ring 36 relative to one another. The operation of the roller drive 30 is further explained by referring to the second roller 32a although screws 32b, 32c and 32d may be present. The skilled person will recognize that instead of three further screws one or two, or even more than three further screws may be used.

The first screw 31 has a longitudinal axis C and the second screw 32a has a longitudinal axis D. Both, the longitudinal axes C and D may be rotation axes of the first and second screws 31, 32a respectively. The longitudinal axes C, D are arranged parallel offset from one another. Therefore the first screw 31 and the second screw 32a are arranged in an off-center relationship relative to one another. The threads of the first and second screws 31, 32a form roller surfaces 40, 41, respectively, which are in contact with each other. The second screw 32a is radially restrained by a bearing 33a, and the further screws 32b, 32c, 32d are radially restrained by bearings 33b, 33c, 33d, respectively. The first screw 31 is radially restrained by the second screw 32a in combination with the further screws 32b, 32c, 32d. Therefore the roller surfaces 40, 41 of the first and second screws 31, 32a are maintained in contact with one another, so that a rotation of one of the first and second screws 31, 32a is transmitted via the contacting roller surfaces 40, 41 by friction to the other one of the first and second screws 31, 32a. Further the outer ring 36 has a roller surface 43 which is arranged for rolling on roller surfaces 42 of the second screw 32a, with the roller surfaces 42, 43 forming a friction transmission. Thus the first screw 31 may be rotated with the outer ring being prevented from rotation, and as a result the first and second screw 31, 32a may displace axially (in a direction parallel to the longitudinal axes C, D) relative to one another. The second screw 32a further is axially coupled with the outer ring 36 so that also the first screw 31 and the outer ring 36 may displace axially relative to one another, when the screw 31 and the outer ring 36 are rotated relative to one another.

Figure 7:
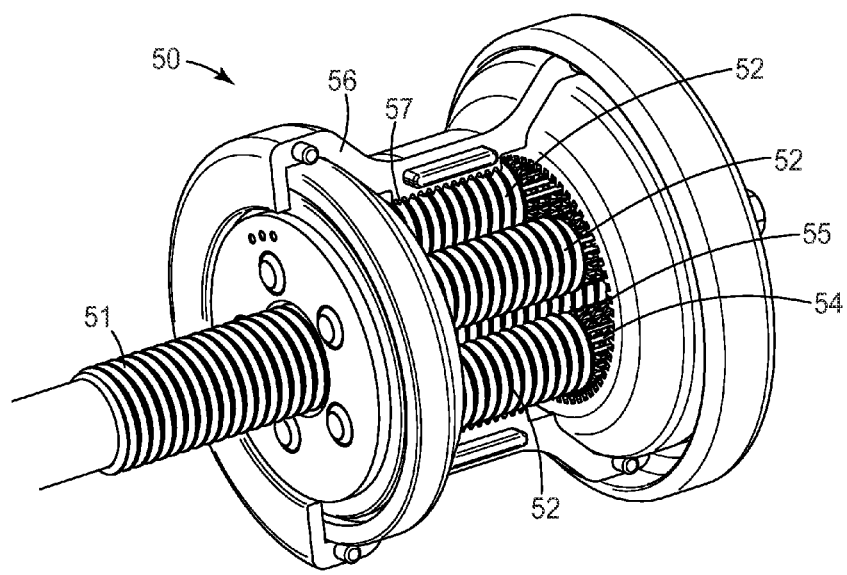
FIG. 7 is a cross-sectional perspective view of a roller drive according to still another embodiment of the invention.

FIG. 7 shows a similar roller drive 50 having a first screw 51 and a plurality of second screws 52 being arranged in a planetary friction transmission relative to one another. Further the roller drive 50 has an outer ring 56 having an inner thread 57. The second screws 52 and the thread 57 of the outer ring 56 are in engagement with one another and coupled via first and second gears 54, 55. Thus a slip between the rotation of the outer ring 56 and the rotation of the second screws in operation of the roller drive is prevented.

In another embodiment (not shown) the first screw may have an axial toothing and a thread which are superposed. Thus the second screw(s) cooperating with the first screw in a planetary arrangement relative to one another may roll on each other with the thread providing for an axial displacement between the first and second screws. Further the second screw(s) may have a toothing for cooperating with the toothing of the first screw so that a slip is prevented during rolling of the first and second screws on one another. The skilled person will recognize that a thread and a toothing superposed with one another may be used in other embodiments of a roller drive, in particular with the embodiment shown in FIG. 2.

Further radial circumferential ribs may be used instead of a thread with at least one of the rollers of the spindle drive. For example a screw with a thread cooperating with a roller having radial circumferential ribs may still provide for an axial displacement between the screw and the rollers. The first and second rollers in any of the embodiments described herein may further guide one another so that the roller drive may be used as a linear guidance in addition to its function as a drive. The guiding effect may further be maximized by urging or pressing the rollers with their roller surfaces on one another.

The axial displacement of any of the embodiments of the roller drive may be used to drive at least a first piston of a dispensing device as illustrated in the following Figures.

Figure 8:
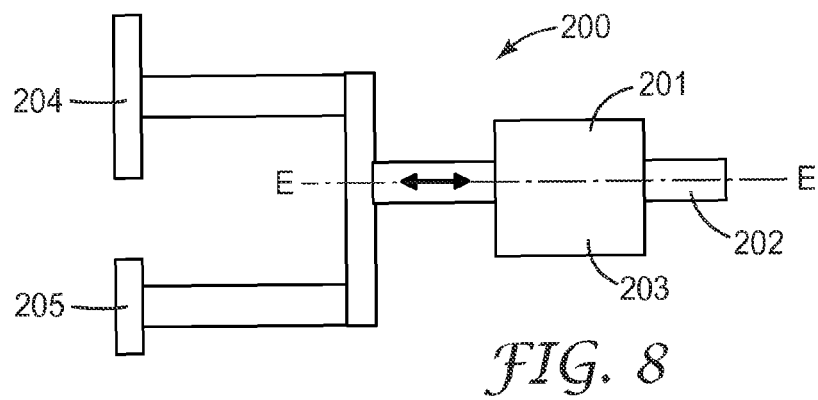
FIG. 8 is a schematic top view of the roller drive arranged in about a center position between two pistons according to an embodiment of the invention.

FIG. 8 shows a device 200 having a roller drive 201. The roller drive has a first roller 202 and a cooperating second roller 203. The second roller 203 is axially fixed in the device and the roller 202 is axially displaceable relative to the second roller by causing the first and second rollers 202, 203 to roll on each other. Thus the first roller 202, which may be a threaded spindle, for example, may be used to displace first and second pistons 204, 205. In FIG. 8 the roller drive has a longitudinal axis E which corresponds to an axis in a direction of the displacement of the first and second rollers 202, 203 relative to each other. The roller drive in this example is arranged with its longitudinal axis E between the first and second pistons 204, 205. Thus one roller drive may be used to drive the two pistons 204, 205. The roller drive may provide for a relatively strong guidance between the first and second rollers. Thus an additional linear guidance may be made unnecessary.

Figure 9:
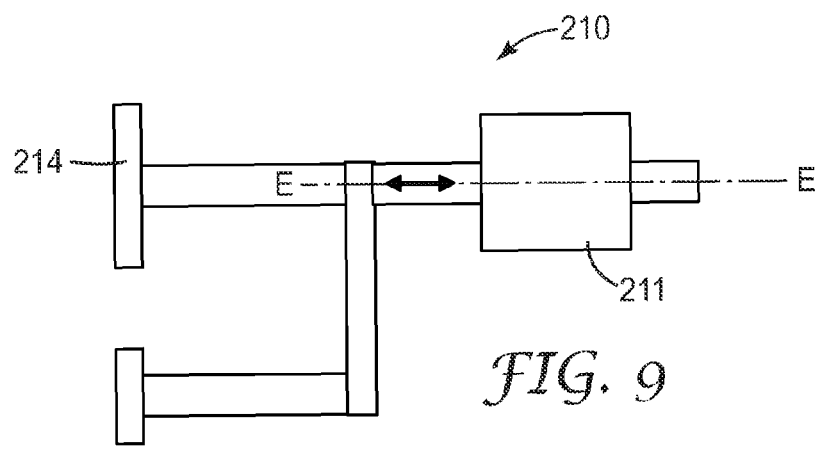
FIG. 9 is a schematic top view of the roller drive arranged inline with a piston according to an embodiment of the invention.
Figure 10:
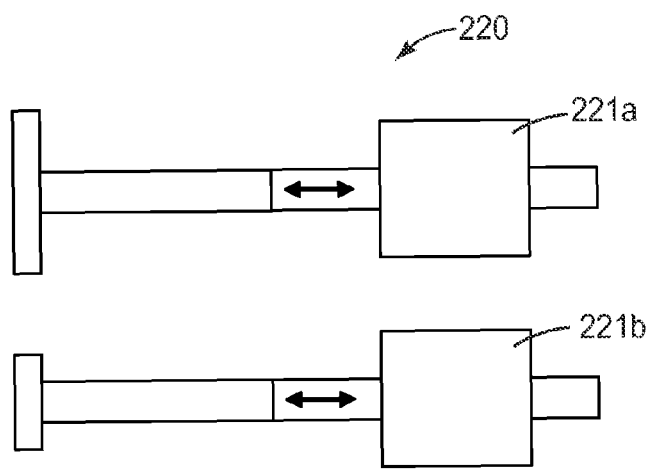
FIG. 10 is a schematic top view of two roller drives each cooperating with a piston according to an embodiment of the invention.

FIG. 9 shows a similar device 210 with the roller drive 211 being arranged with its longitudinal axis E inline with a longitudinal axis of a piston 214. And FIG. 10 shows a device 220 having two roller drives 221a, 221b.

Figure 11:
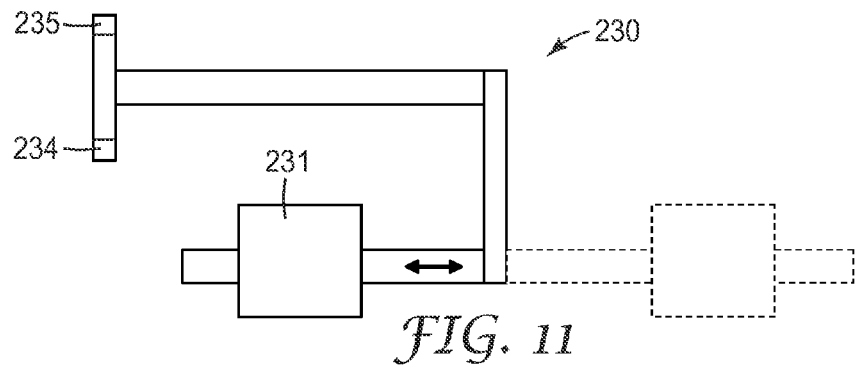
FIG. 11 is a schematic side view of the roller drive arranged below two pistons according to an embodiment of the invention.

In FIG. 11 a device 230 is shown in which a roller drive 231 is arranged below pistons 234, 235 (piston 235 is partially covered by piston 235 in this view). For example the roller drive 231 may be arranged generally parallel to the pistons 234, 235 as illustrated, or inline but radially offset as indicated by the dashed lines.

Figure 12:
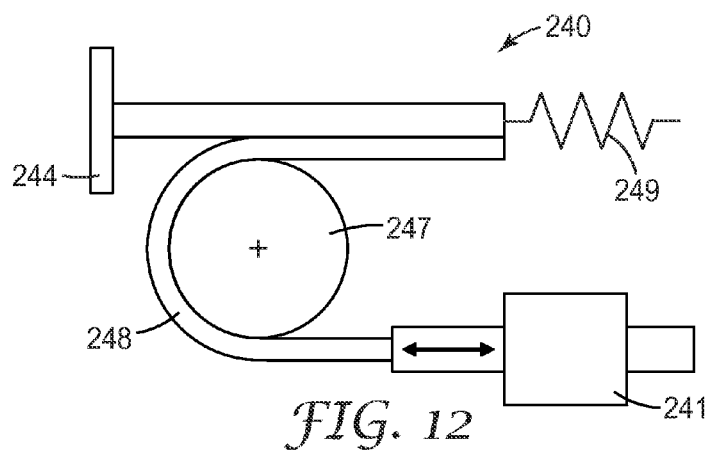
FIG. 12 is a schematic side view of the roller drive cooperating via a belt with a piston according to an embodiment of the invention.

FIG. 12 shows a device 240 with a roller drive 241 that is coupled to a piston 244 via a belt 248. The roller drive 241 may be arranged in the device for pulling the belt and thus for pulling the piston in one direction. The piston may be returned by a return spring 249. As illustrated the belt may be deflected by a roll 247, but may in another example be used without a deflection. Therefore the belt may allow the roller drive to be arranged at different positions in the device as desired. Thus a relatively compact design may be enabled.

Figure 13:
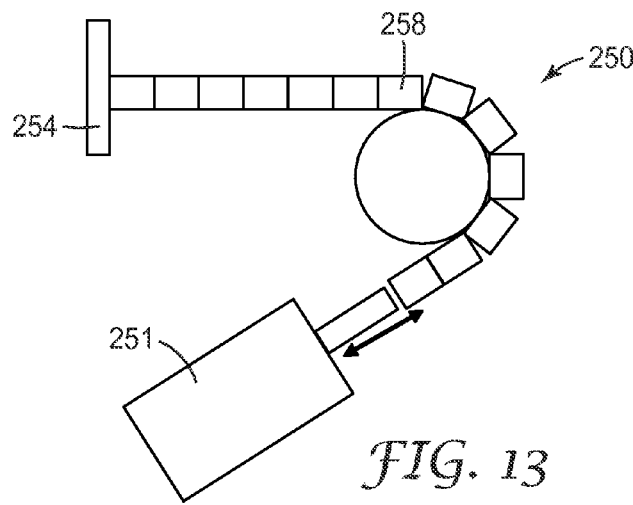
FIG. 13 is a schematic side view of the roller drive cooperating via a push-pull chain with a piston according to an embodiment of the invention.

FIG. 13 shows a similar device 250 in which a roller drive 251 drives a piston 254 via a push-pull chain 258. Such a push-pull chain preferably transmits forces when pushed and when pulled so that a return spring may not be necessary.

Figure 14:
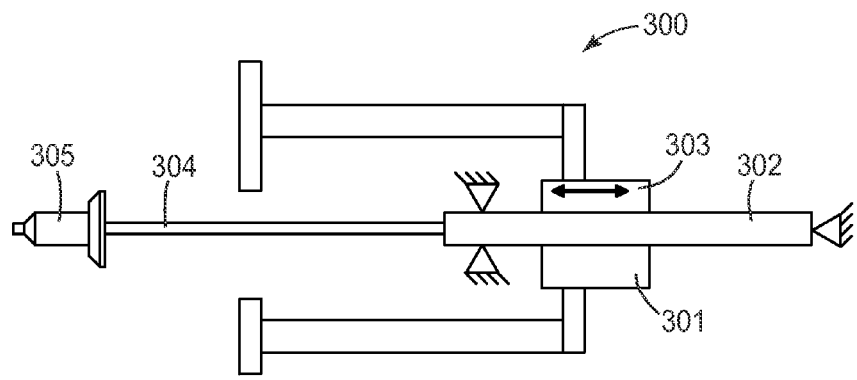
FIG. 14 is a schematic top view of the roller drive for driving two pistons and a mixer shaft according to an embodiment of the invention.

FIG. 14 shows a device 300 having a roller drive 301 in which a first roller 302 (for example a spindle) is axially fixed relative to the device and a second roller 303 being displaceable by the roller drive 301. The embodiment generally corresponds to the embodiment shown in FIG. 8. However a mixer shaft 304 for driving a mixer 305 is coupled to the first roller 302. Therefore when the first roller 302 is rotated for displacing the second roller 301 the mixer shaft will also be rotated, which thus drives the mixer.

Figure 15:
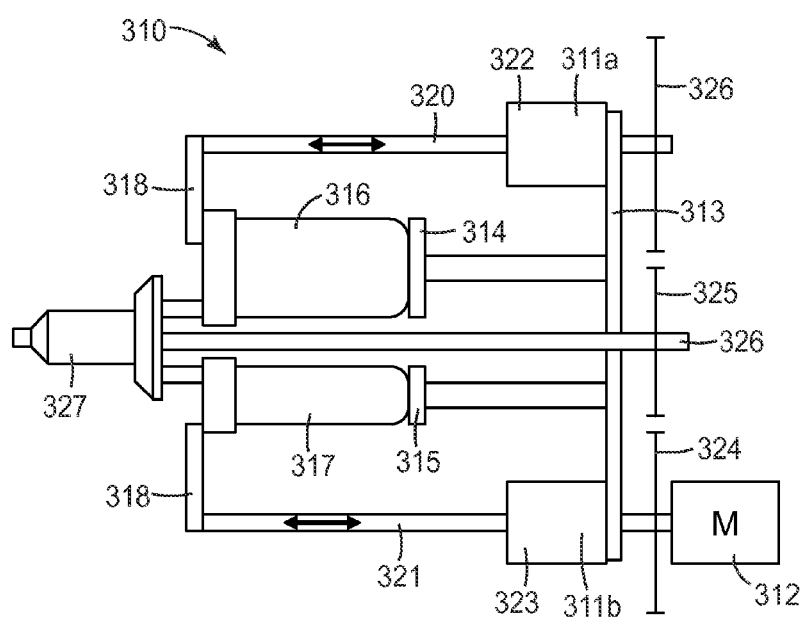
FIG. 15 is a schematic top view of two roller drives implemented in a device according to an embodiment of the invention.

FIG. 15 shows an exemplary device 310 having two roller drives 311a, 311b for driving a traverse 313. The traverse carries a first piston 314 and a second piston 315. Further the device comprises first and second containers 316, 317. The first and second pistons 314, 315 are arranged for pressurizing the first and second containers 316, 317 respectively. Thereby a first and a second component may be extruded from the first and second containers 316, 317 respectively. In the example the containers are foil bags which may be compressed to extrude the components. The foil bags may therefore be accommodated in cartridges which may radially support the foil bags during compression. However in another example the containers may be formed by cartridges in which displaceable pistons for extruding the components are arranged. In the example the containers are pressurized against a pressure plate 318.

The roller drives 311a, 311b in the example have first rollers 320, 321 respectively. The first rollers 320, 321 and the pressure plate 318 are axially retained. Further the roller drives 311a, 311b have second rollers 322, 323 respectively. The second rollers 322, 323 and the traverse are axially retained. Therefore in operation of the first and second roller drives 311a, 311b the traverse (together with the pistons 314, 315) may be moved toward the pressure plate 318 with the containers pressurized between.

The device 310 has one motor 312 which via gears 324, 325, 326 drives the first rollers 320, 321. Further the gear 325 drives a mixer drive 326 for driving a mixer 327. Thus a device may be provided having a minimized number of parts, but providing a relatively comfortable functionality. In particular such a device may have only one motor. Further the device may not have a complex gear box and/or additional linear guides, and may thus be relatively inexpensive.

Figure 16:
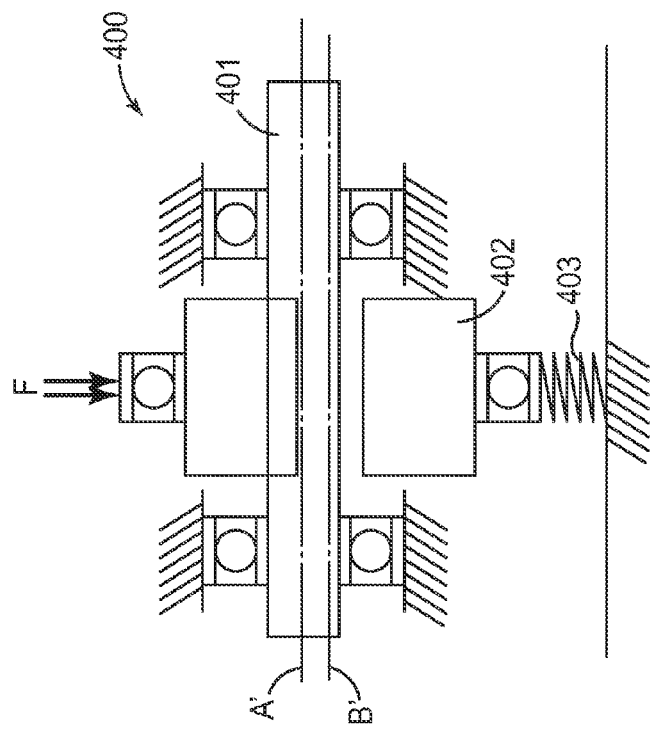
FIG. 16 is a schematic view of an alternative roller drive in a first operating mode according to an embodiment of the invention.

FIG. 16 shows a roller drive 400 having a first roller in the form of a threaded screw 401 and a second roller in the form of a hollow threaded nut 402. The screw 401 and the nut 402 are sized such that a play is provided between the cooperating threads. Further in this example the threads of the screw 401 and the nut 402 are dimensioned such that the smallest inner diameter of the thread of the nut is smaller than the largest outer diameter of the thread of the screw. Thus the screw 401 and the nut 402 in any position between an off-center and a center position relative to each other engage with their threads. In the situation shown the roller drive 400 operates in a first operating mode in which the screw 401 and the nut 402 are urged toward an off-center relationship relative to one another by a force F. Thus the operation of the roller drive 400 in the first operation mode generally corresponds to the operation of the example shown in FIG. 2.

Figure 17:
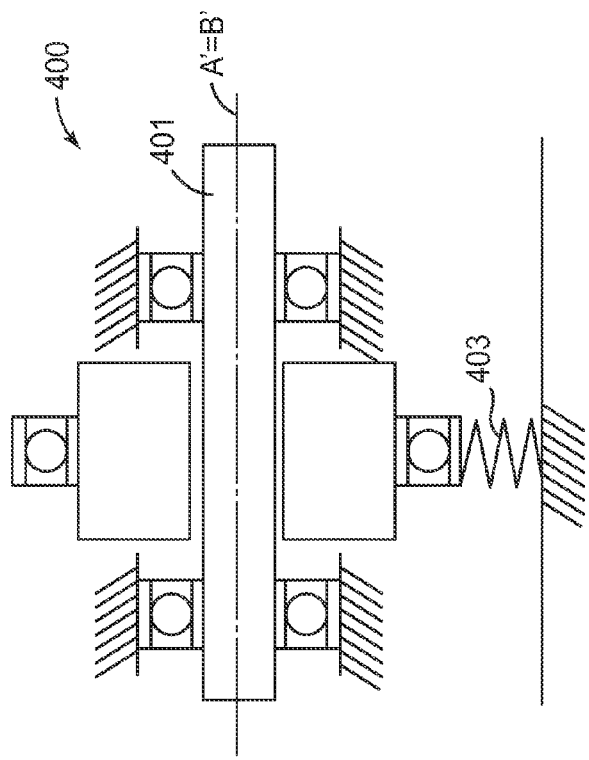
FIG. 17 is a schematic view of the alternative roller drive shown in FIG. 16 in a second operating mode.

FIG. 17 shows the same roller drive 400 in a second operating mode in which the radial force F suspended. The screw 401 and the nut 402 therefore preferably align centrically to each other. Therefore in the first operating mode the roller drive 400 preferably operates with the threads predominantly rolling on each other, whereas in the second operating mode the threads predominantly slide on each another. Accordingly in the first operating mode the axial displacement speed of the screw and the nut relative to each other is preferably smaller than the axial displacement speed in the second operating mode at the same rotation speed of the screw and the nut relative to each other. In the example a spring 403 is arranged for urging the nut toward a center relationship with the screw. Further a rotation stop (not shown) for the nut may be provided. Thus the screw 401 may by rotated and the nut 402 may be prevented from rotating so that an axial movement between the screw 401 and the nut 402 can be caused. The skilled person will recognize that in the first operating mode such a rotation stop is preferably suspended to allow a rolling of the threads on each other which in some embodiments requires the nut and the screw to rotate.

The invention claimed is:

1. A device for dispensing a dental composition, comprising a first piston for extruding at least a component of the dental composition from a first container, and a roller drive for displacing the first piston, the roller drive comprising a first roller and a cooperating second roller, each of the first and the second rollers having a roller surface comprising a radial rib profile, and further each of the first and the second rollers having first and second longitudinal axes, respectively, that are arranged in an off-center relationship relative to one another, wherein the first and second rollers are arranged for rolling with their roller surfaces on one another, with the rib profiles engaging one another.

2. The device of claim 1, wherein the rib profile of at least one of the first and second rollers is formed by a screw thread.

3. The device of claim 2, wherein the rib profile of the other one of the first and second rollers is formed by at least one closed circumferential rib.

4. The device of claim 1, in which the first and second rollers are adapted such that rolling of the first and second rollers on one another causes the first and second rollers to displace in a direction laterally to a direction of the rolling.

5. The device of claim 1, wherein the roller surfaces of the first and second rollers have different circumferences.

6. The device of claim 1, wherein the first roller surface has a first diameter and the second roller surface has a cooperating second thread diameter, wherein the first and second diameters are different.

7. The device of claim 1, in which the first and second rollers are in an epicyclic or a planetary roller arrangement.

8. The device of claim 7, in which the first roller has an outer rib profile and the second roller forms a hollow roller with an inner rib profile, wherein the first roller forms a planetary roller within the hollow second roller.

9. The device of claim 7, in which the first and second rollers both have an outer rib profile, wherein the first roller forms a sun roller and the second roller forms a planetary roller around the sun roller.

10. The device of claim 9, having at least one further planetary rollers.

11. The device of claim 1, comprising at least one of a belt, a chain, and a push-pull chain for transmitting a displacement of the roller drive to cause the piston to displace.

12. The device of claim 1, comprising a second piston for extruding a second component from a second container, and being adapted to receive and drive a dynamic mixer for continuously mixing the first and second component as they are extruded from the first and second containers.

13. The device of claim 12, having a motor for driving the roller drive and a mixer shaft for driving the mixer.

14. The device of claim 12, comprising one roller drive for driving the first and the second pistons, or two roller drives each for driving one of the first and second pistons.

15. A device for dispensing a dental composition, comprising a first piston for extruding at least a component of the dental composition from a first container, and a roller drive for displacing the first piston, the roller drive comprising a first roller in the form of a threaded screw and a cooperating second roller in the form of a hollow threaded nut, each of the threaded screw of the first roller and the hollow threaded nut of the second roller having a thread which provides a roller surface, and further each of the first and the second rollers having first and second longitudinal axes, respectively, wherein the device is adapted such that the roller drive can be operated in a first operating mode and a second operating mode,
   wherein in the first operating mode the threaded screw and the hollow threaded nut are positioned with the first and second longitudinal axes arranged in an off-center relationship relative to one another, and with the first and second rollers arranged for rolling with their roller surfaces on one another; and
   in the second operating mode the threaded screw and the hollow threaded nut are positioned with the first and second longitudinal axes substantially arranged in a center relationship relative to one another, and with the first and second rollers arranged for sliding with their roller surfaces on one another;
   wherein in the first and second operating modes the threads engage one another.

16. A device for dispensing a dental composition, comprising:
   a first piston for extruding at least a component of the dental composition from a first container; and a roller drive for displacing the first piston, the roller drive comprising a first roller and a cooperating second roller, each of the first and the second rollers having a roller surface comprising a radial rib profile, and each of the first and the second rollers having first and second longitudinal axes, respectively, that are arranged in an off-center relationship relative to one another, wherein the first and second rollers are arranged for rolling with their roller surfaces on one another, with the rib profiles engaging one another;
   wherein the first and second rollers are adapted such that rolling of the first and second rollers on one another causes the first and second rollers to displace in a direction laterally to a direction of the rolling, wherein the first roller surface has a first diameter and the second roller surface has a cooperating second thread diameter, wherein the first and second diameters are different, and wherein the first roller has an outer rib profile and the second roller forms a hollow roller with an inner rib profile, wherein the first roller forms a planetary roller within the hollow second roller.

17. The device of claim 16 further comprising a second piston for extruding a second component from a second container, and being adapted to receive and drive a dynamic mixer for continuously mixing the first and second component as they are extruded from the first and second containers.

* * * * *

UNITED STATES PATENT AND TRADEMARK OFFICE
CERTIFICATE OF CORRECTION

| | |
|---|---|
| PATENT NO. | : 8,814,738 B2 |
| APPLICATION NO. | : 13/510550 |
| DATED | : August 26, 2014 |
| INVENTOR(S) | : Jens Gramann et al. |

Page 1 of 1

It is certified that error appears in the above-identified patent and that said Letters Patent is hereby corrected as shown below:

In the Specification

<u>Column 2</u>

Line 9, delete "another" and insert -- another. --, therefor.

<u>Column 11</u>

Line 3, delete "may by" and insert -- may be --, therefor.

In the Claims

<u>Column 11</u>

Line 50, in Claim 10, delete "rollers." and insert -- roller. --, therefor.

Signed and Sealed this
Fifth Day of May, 2015

Michelle K. Lee
*Director of the United States Patent and Trademark Office*